United States Patent
Hansen

[11] Patent Number: 5,678,736
[45] Date of Patent: Oct. 21, 1997

[54] PLASTIC CONTAINER FOR FLOWABLE MATERIALS AND METHOD FOR MANUFACTURE THEREOF

[76] Inventor: Bernd Hansen, Heerstrasse 16, D-74429 Sulzbach-Laufen, Germany

[21] Appl. No.: 424,798

[22] Filed: Apr. 19, 1995

[30] Foreign Application Priority Data

Jun. 14, 1994 [DE] Germany .................. 44 20 594.5

[51] Int. Cl.⁶ .................................................. B65D 37/00
[52] U.S. Cl. .................... 222/209; 222/212; 222/215; 222/389; 222/541.6
[58] Field of Search ................... 222/206, 209, 222/212, 215, 386, 389, 541.6, 541.7, 541.9

[56] References Cited

U.S. PATENT DOCUMENTS

| | | | |
|---|---|---|---|
| 738,009 | 9/1903 | Dews | 222/95 X |
| 3,124,171 | 3/1964 | Mitchell | 222/209 X |
| 3,154,116 | 10/1964 | Mitchell | 222/209 X |
| 3,184,120 | 5/1965 | Undi | 222/389 X |
| 3,442,424 | 5/1969 | Prussin et al. | 222/389 X |
| 3,993,223 | 11/1976 | Welker, III et al. | 222/541.9 X |
| 4,248,227 | 2/1981 | Thomas | 222/541.6 X |
| 4,413,754 | 11/1983 | Landwehr et al. | 222/541.6 X |
| 4,563,104 | 1/1986 | Saint-Amand | 222/209 X |
| 5,048,727 | 9/1991 | Vlasich | 222/209 |
| 5,052,588 | 10/1991 | Schlosser | 222/541.6 X |
| 5,121,856 | 6/1992 | Weiler et al. | 222/209 |

FOREIGN PATENT DOCUMENTS

| | | | |
|---|---|---|---|
| 1207862 | 12/1965 | Germany | 222/389 |
| 298008 | 4/1954 | Switzerland | 222/389 |

*Primary Examiner*—Kevin P. Shaver
*Attorney, Agent, or Firm*—Roylance, Abrams, Berdo & Goodman. L.L.P.

[57] ABSTRACT

A plastic container for apportionable delivery of flowable, especially pasty materials, has a discharge opening at one end and a self-contained chamber only open to the inside of the container at the other end. The chamber volume is reducible by manual deformation. The chamber is configured in one piece with the container body. The container body is configured as a cylinder. The inside space of the container body receiving the flowable material is separated from the inner volume of the chamber by a separator piston longitudinally slidable in the container body.

13 Claims, 1 Drawing Sheet

PLASTIC CONTAINER FOR FLOWABLE MATERIALS AND METHOD FOR MANUFACTURE THEREOF

FIELD OF THE INVENTION

The present invention relates to a plastic container for apportionable delivery of flowable, especially pasty materials. The present invention also relates to a method for the manufacture of such a container.

BACKGROUND OF THE INVENTION

Known containers of this type can receive and discharge salves in portions and are configured as ampules. In each container, a bellows filled with air is constructed at the container end opposite the delivery opening. For delivery of the salve, the discharge opening of the ampule is opened and the bellows is pressed together. Air pressed out of the bellows pushes the salve out of the ampule.

In this arrangement, however, an air channel can be formed through the salve or along the inside wall of the ampule, which results in a more or less major portion of the contents of the ampule not being pressed out of the ampule. The air channel formation disadvantageously causes great variation in the quantity of material being delivered due to imprecise apportioning. Additionally, particularly significant with expensive products, the residual quantities of material are lost.

SUMMARY OF THE INVENTION

Objects of the present invention involve providing a plastic container for apportionately dispensing of flowable materials that ensures that the contents can be nearly completely discharged through the discharge opening, and that can be easily manufactured at low cost.

The foregoing objects are basically obtained by a plastic container for apportionately dispensing of flowable materials, comprising a cylindrical container body defining an inside space receiving flowable material and having first and second opposite ends. A discharge opening is formed at the first end of the container body. A self-contained chamber, formed unitarily with the container body, opens only into the inside space of the container body at the second end of the container body, and has an inner volume reducible by manual deformation. A separating piston is longitudinally slidable in the inside space of the container body, and separates the inner volume of the chamber from the inside space of the container body.

The material carried in the container body will be pressed against the discharge opening by means of the separator piston. Thus, only a thin film of the material carried in the container adheres and remains on the inside wall of the container body in case it is needed. Also, the end of the container body forming the discharge opening and the surface of the separator piston facing this end opening can be configured so that only a negligible amount of residue is left behind. A very high degree of apportioning precision can then be attained. The container, according to the present invention, can be manufactured at very low cost, especially since it has only two parts, i.e., the container body with the chamber and the separator piston.

The manufacturing cost can be kept very low. Thus, the container according to the present invention has a considerably lower cost, relative to, for example, an injection molded container of the same dimensions.

The separator piston can be an inserted part made of plastic. The plastic can be the same plastic as the container body. This has the advantage that the material carried in the container does not come into contact with different materials. Polyfluoroethylene is especially advantageous, since it is inert. Polyethylene and polypropylene can also be used.

Advantageously, the outside contour of the separator piston is adaptively fit to the preferably circular cylindrical inside contour of the container body. To avoid the piston becoming difficult to move because of any unfavorable tolerance situation, according to one preferred embodiment, at least one self-contained packing washer is constructed on the separator piston. That packing washer then engages with slight pressure on the inside wall of the cylindrical container body. Other packing means can also be considered, for instance, an O-ring. Packing means constructed on the separator piston, such as the cited packing washer, however are more advantageous from a cost outlay point of view. Whether packing means can be entirely omitted depends primarily on the properties of the material to be controlled and the thrusting force of the separator piston.

The chamber constructed at one end of the container body can be configured as a bellows and can extend longitudinally in the same direction as the container body. With such bellows, the separator piston can be arranged at one end of a piston rod which projects into the bellows and which can be thrust outwardly toward the discharge opening when the bellows is pressed together in axial direction.

The chamber can also be configured as a bellows which can be pressed together transverse to the longitudinal alignment of the container. The separator piston is then thrust by means of the air in the bellows, which air can be pressed out of the bellows. The volume of the bellows must be sufficiently great to execute the action.

Preferably the container is closed by a break-off closing at the end forming the discharge opening. The break-off closing can be separated from the discharge opening along a break line by tipping or rotating the closing relative to the container body.

Other objects of the present invention involve providing a method for manufacturing a plastic container for apportionately dispensing flowable materials which is simple and inexpensive to perform and produces a reliable container.

The foregoing objects are also basically obtained by a method for manufacturing a plastic container for apportionately dispensing flowable materials, comprising the steps of shaping plastic material into a cylindrical container body by blow molding with a discharge opening at a first longitudinal end of the container body, forming a seal to close the discharge opening at the first longitudinal end of the container body, filling an inside space of the container body with flowable material, inserting a separating piston in the inside space of the container after filling with flowable material, forming a self-contained chamber opening only into the inside space of the container body at a second longitudinal end opposite the first longitudinal end of the container body by blow molding, and sealing the container closed.

The container is manufactured by this method, including its break-off closing and the chamber, preferably from an extruded tube segment in a blow molding machine. In the blow molding machine, the container is filled, is completed with the separator piston and is then closed. All surfaces coming into contact with the material introduced into the container are antiseptic, the same as the sterilized air enclosed in the chamber, because the temperature required for blow molding is sufficiently high.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which form a part of this disclosure.

DETAILED DESCRIPTION OF THE INVENTION

A plastic ampule for apportionable delivery of or apportionately dispensing its flowable material contents, for instance, a pharmaceutical or cosmetic salve, has a right circular cylindrical ampule body 1. Body 1 is configured at one end in the shape of a hemisphere and here has a circular discharge opening.

The discharge opening is closed by means of a break-off closing 2. Break-off closing 2 is provided with a flat toggle 3, which can be grasped with two fingers to facilitate application of the breaking force. Break-off closing 2 is separated from ampule body 1 along a break line 4 of diminished wall thickness. Break line 4 extends along the border or periphery of the circular discharge opening. Following the removal of break-off closing 2, the discharge opening is free or open, and forms a central opening in the hemispherical end part of ampule body 1.

The other end of ampule body 1 is constructed with a one-piece, rectangular chamber 5. Chamber 5 extends longitudinally in the same direction as ampule body 1, and is limited by or defined between thin walls. The thin walls can be pressed together with two fingers to collapse the chamber. The chamber volume is at least as great as the volume of the material contents to be pressed and forced out of the ampule.

Figure 2:
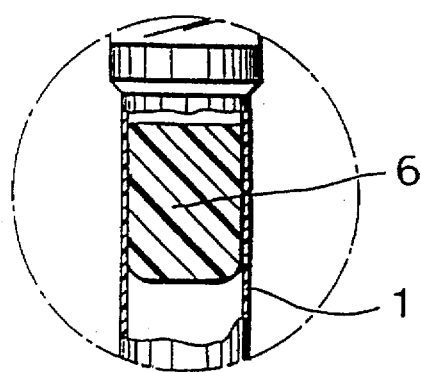
FIG. 2 is a partial, enlarged, side elevational view in section of the container of FIG. 1.
Figure 1:
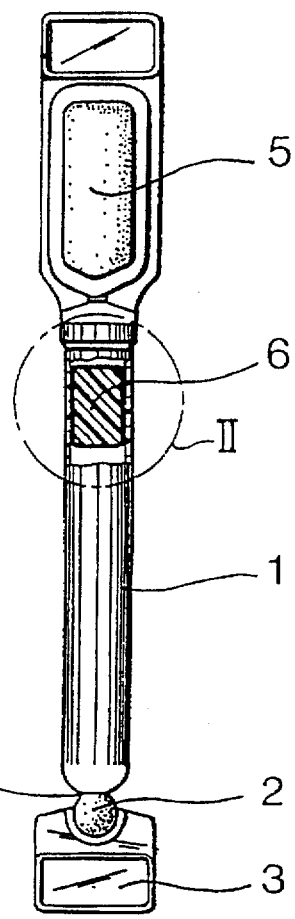
FIG. 1 is a side elevational view, partially in section, of a container according to a first embodiment of the present invention.

Referring initially to FIGS. 1 and 2, the material filling ampule body 1 is separated from the inside space of chamber 5 and the air contained in the chamber inside space by a separator piston 6. Separator piston 6 is arranged to be longitudinally slidable in ampule body 1. The piston outer or cover surface engages on the inside surface of ampule body 1 or, for tolerance purposes, has a transverse cross-section diameter which is approximately 0.4 mm to 0.8 mm smaller than the inside diameter of ampule body 1. Separator piston 6 has a right circular cylindrical configuration. At the piston end directed toward the discharge opening, the contact surface of the piston surface is rounded off on the frontal surface to permit separator piston 6 to extend into the hemispherical end segment of ampule body 1. This enables the piston to press almost all of the material contained in ampule body 1 out through the discharge opening.

The ampule then consists of only two separate parts. The parts are preferably manufactured of the same plastic, for instance polyethylene or polypropylene. Separator piston 6, however, can be made of polyfluoroethylene, known commercially as Teflon, since this material is inert.

After break-off closing 2 is removed, the walls defining chamber 5 are pressed together, and are deformed to decrease the chamber volume. The walls of chamber 5 are of such dimensions that the force required for this deformation can be applied without any difficulty transverse to the chamber longitudinal direction with two fingers. The air forced out of chamber 5 forces separator piston 6 from the position illustrated in FIG. 1 toward the discharge opening of ampule body 1. Separator piston 6 moves the material contained in ampule body 1 and in front of the piston. If desired, a thin film of material remains adhering to the inside surface of ampule body 1. The volume of chamber 5 is of sufficient magnitude that separating piston 6 can be moved forward until it engages the hemispherical end of ampule body 1. In this manner, only a very small residual quantity of material remains in ampule body 1.

The manufacture, filling and sealing of the ampule is executed in a blow molding machine. First, ampule body 1 and break-off closing 2 are formed by blow molding. Second, ampule body 1 is filled with a predetermined quantity of the material to be stored in the ampule. Separating piston 6 is mechanically inserted into ampule body 1, after the material. Finally, ampule body 1 is sealed securely by the construction of chamber 5.

Preferably, separating pistons 6 are produced in the same blow molding machine for manufacturing the ampules, and are produced out of an area of the material being used in the blow molding which would accumulate during ampule manufacture as waste material. The separating piston is formed by hollow drawing of this waste material. In other words, the piston is formed in the same manner as the ampule. It is then stamped out of the material surrounding it. A configuration of a packing washer can be left on the separating piston. The packing washer cross section is then guided in the space between the ampule body inside surface and the separating piston. Separating pistons manufactured in this manner are transported in a magazine of the blow molding machine. From the magazine, the pistons are removed for insertion in the later formed ampules.

Figure 3:
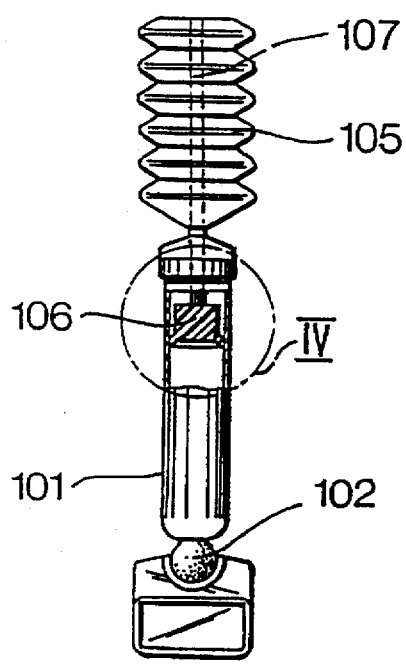
FIG. 3 is a side elevational view, partially in section, of a container according to a second embodiment of the present invention.
Figure 4:
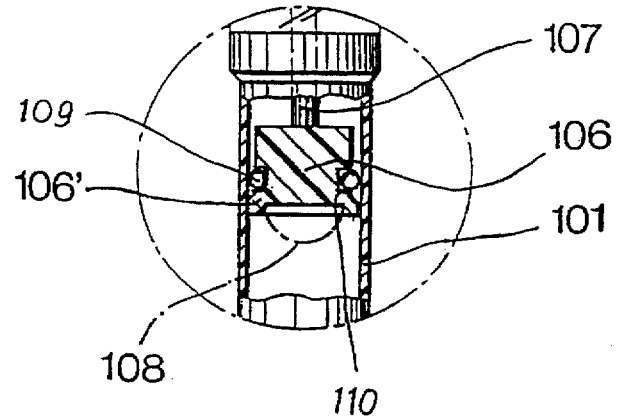
FIG. 4 is a partial, enlarged side elevational view in section of the container of FIG. 3.

In the second exemplary embodiment of the container according to the present invention, shown in FIGS. 3 and 4, an ampule includes ampule body 101 and a break-off closing 102, configured in the same manner as ampule body 1 and break-off closing 2 of the first embodiment. As in the first embodiment, a separator piston 106 is inserted into ampule body 101. Separator piston 106 is mounted on a piston rod 107 constructed in one piece or unitarily with the piston. Piston rod 107 projects coaxially from ampule body 101 and extends beyond the ampule end opposite break-off closing 102. This projecting segment of piston rod 107 lies inside a bellows 105. Bellows 105 is also constructed coaxial to ampule body 101, on the ampule end opposite break-off closing 102. The bellows is formed similarly to chamber 5 of the first embodiment, and is formed in one piece or unitarily with the ampule body.

If bellows 105 is pressed together or compressed in an axial direction, air thrust out of bellows 105 and a thrusting force exerted on piston rod 107 forces separator piston 106 toward the discharge opening. Thus, separator piston 106 can be easily moved against the discharge opening of ampule body 101. The separator piston engages with a certain level of friction on the inside wall of ampule body 101. The end of separator piston 106 directed toward the discharge opening is constructed with a self-contained, flexible packing washer 106'.

Washer 106' engages on the inside wall surface of ampule body 101. Since packing washer 106' extends radially outwardly further than separating piston 106, adjacent the discharge opening, the washer becomes progressively more forcefully pressed against the inside wall surface of ampule body 101 the greater the pressure applied on the material contained in ampule body 101. During longitudinal thrusting of separating piston 106, packing washer 106' practically completely wipes off the material adhering to the inside wall of ampule body 101. The material in hemispherical end of ampule body 101 is also to be emptied as extensively as possible. Thus, a hemispherical salient or projection 108 can be formed on the front end of separating piston 106, bordered by packing washer 106', as shown in FIG. 4 with a broken line.

As in the first embodiment shown in FIGS. 1 and 2, the second embodiment shown in FIGS. 3 and 4, has two parts which incorporate the ampule preferably of identical material, for example, polyethylene or polypropylene. If needed, separating piston 106 with its piston rod 107 can also be of polyfluoroethylene.

The second embodiment is also particularly advantageous when manufactured in a blow molding machine. The steps used in the method are the same as those described for the first embodiment.

Separating piston 106 could be configured without packing washer 106', i.e., the same as separating piston 6 of the first embodiment. Likewise, separating piston 6 of the first embodiment could be provided with a flexible packing washer and/or a hemispherical salient as embodied in the salient 108. Furthermore, the separating piston can have either only a packing washer or, in addition to the washer, a packing element in the form of an O-ring. However, the O-ring would increase the costs which is at a minimum when the ampule is made of only two parts and is manufactured according to the method of the present invention. O-ring 109 lies in a groove 110 of piston 106.

While various embodiments have been chosen to illustrate the invention, it will be understood by those skilled in the art that various changes and modifications can be made therein without departing from the scope of the invention as defined in the appended claims.

What is claimed is:

1. A plastic container for apportionately dispensing flowable materials, comprising:
   a cylindrical container body defining an inside space receiving flowable material and having first and second opposite ends;
   a discharge opening at said first end of said container body;
   an air passage at said second end of said container body;
   a self-contained chamber defined between thin walls and opening only into said inside space of said container body through said air passage at said second end of said container body, said chamber having a predetermined, set inner volume filled with air and reducible by manual deformation of said thin walls, said chamber formed unitarily with said container body; and
   a separating piston longitudinally slidable in said inside space of said container body, and separating said air passage and said inner volume of said chamber from said inside space of said container body.

2. A plastic container according to claim 1 wherein said separating piston is inserted in said container body and consists of plastic.

3. A plastic container according to claim 1 wherein said separating piston comprises a self-contained packing washer.

4. A plastic container according to claim 1 wherein said separating piston comprises an annular, radially opening groove and an O-ring located in said groove and engaging an inside surface of said container body.

5. A plastic container according to claim 1 wherein said chamber comprises a bellows coaxially aligned with said container body.

6. A plastic container according to claim 5 wherein said bellows comprises a piston rod coupled to said separating piston, such that compression of said bellows forces said piston rod and said separating piston toward said discharge opening.

7. A plastic container according to claim 6 wherein said piston rod and said separating piston are unitary.

8. A plastic container according to claim 1 wherein said chamber comprises a bellows which is coaxially aligned with said container body along a longitudinal axis and which can be compressed in a direction transverse to said longitudinal axis.

9. A plastic container according to claim 1 wherein a break-off closing is sealed to said first end of said container body to close said discharge opening.

10. A plastic container according to claim 2 wherein said chamber comprises a laterally collapsible bellows coaxially aligned with said container body.

11. A plastic container according to claim 1 wherein said chamber is generally in the form of a rectangular block.

12. A plastic container according to claim 1 wherein said air passage has transverse cross-sectional dimensions less than corresponding transverse cross-sectional dimensions of said inside space and said inner volume.

13. A plastic container according to claim 1 wherein said inner volume is at least as great as a volume of said flowable material to be pressed and forced out of said container body.

* * * * *